US006701183B2

(12) United States Patent
Baker et al.

(10) Patent No.: US 6,701,183 B2
(45) Date of Patent: Mar. 2, 2004

(54) LONG TERM ATRIAL FIBRILLATION MONITOR

(75) Inventors: Robert L. Baker, Ann Arbor, MI (US); Jack E. Lohman, Colgate, WI (US)

(73) Assignee: Lechnolgies, LLC, Pewaukee, WI (US)

( * ) Notice: Subject to any disclaimer, the term of this patent is extended or adjusted under 35 U.S.C. 154(b) by 237 days.

(21) Appl. No.: 09/827,551

(22) Filed: Apr. 6, 2001

(65) Prior Publication Data

US 2002/0147409 A1 Oct. 10, 2002

(51) Int. Cl.⁷ .............................. A61B 5/046; A61N 1/39
(52) U.S. Cl. ............................................ 600/518; 607/5
(58) Field of Search .................. 607/4–8; 600/509–518

(56) References Cited

U.S. PATENT DOCUMENTS

| | | | |
|---|---|---|---|
| 3,608,545 A | | 9/1971 | Novack et al. |
| 3,938,507 A | * | 2/1976 | Sarnoff et al. ............... 600/514 |
| 4,004,577 A | | 1/1977 | Sarnoff |
| 4,576,170 A | * | 3/1986 | Bradley et al. ............... 607/27 |
| 4,596,256 A | * | 6/1986 | Ascher et al. ............... 600/523 |
| 5,172,698 A | * | 12/1992 | Stanko ........................ 600/510 |
| 5,207,219 A | | 5/1993 | Adams et al. |
| 5,226,425 A | * | 7/1993 | Righter ........................ 600/523 |
| 5,282,837 A | | 2/1994 | Adams et al. |
| 5,321,618 A | * | 6/1994 | Gessman ........................ 607/5 |
| 5,339,824 A | | 8/1994 | Engira |
| 5,350,404 A | | 9/1994 | Adams et al. |
| 5,586,556 A | * | 12/1996 | Spivey et al. ............... 600/510 |
| 5,772,604 A | * | 6/1998 | Langberg et al. ............ 600/518 |
| 5,928,141 A | * | 7/1999 | Castelli ........................ 600/372 |
| 6,345,196 B1 | * | 2/2002 | Castelli ........................ 600/509 |
| 6,363,274 B1 | * | 3/2002 | Scalisi et al. ................ 600/523 |
| 6,427,083 B1 | * | 7/2002 | Owen et al. .................... 607/5 |
| 6,487,442 B1 | * | 11/2002 | Wood .......................... 600/515 |

FOREIGN PATENT DOCUMENTS

GB 2083915 A 3/1982

OTHER PUBLICATIONS

Medisana, Instructions for Cardiocheck, 7 pages,.
Professor Dr. med. Bernd Kronig, Medisana, Importance of Patient Self–Measurement, 8 pgs., Sep. 9, 1999.
Medisana Cardiocheck Self–EKG , 1–2.

* cited by examiner

Primary Examiner—Jeffrey R. Jastrzab
(74) Attorney, Agent, or Firm—Quarles & Brady LLP

(57) ABSTRACT

An atrial fibrillation monitor provides hand-contacting electrodes to allow daily ECG measurements of a patient without cumbersome electrode connection to the patient. ECG data may be diagnosed by the monitor to indicate likelihood of atrial fibrillation and an indication provided to the patient ECG data based on that indication may be forwarded to a physician or other healthcare professional for a review.

20 Claims, 2 Drawing Sheets

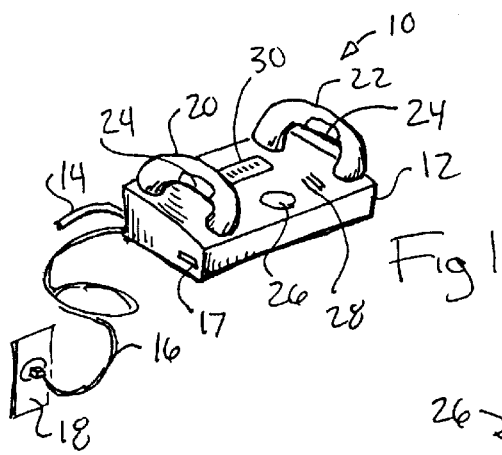
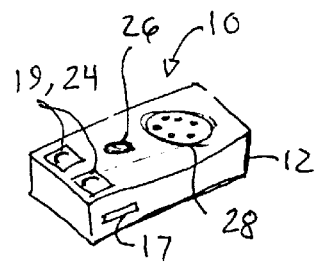
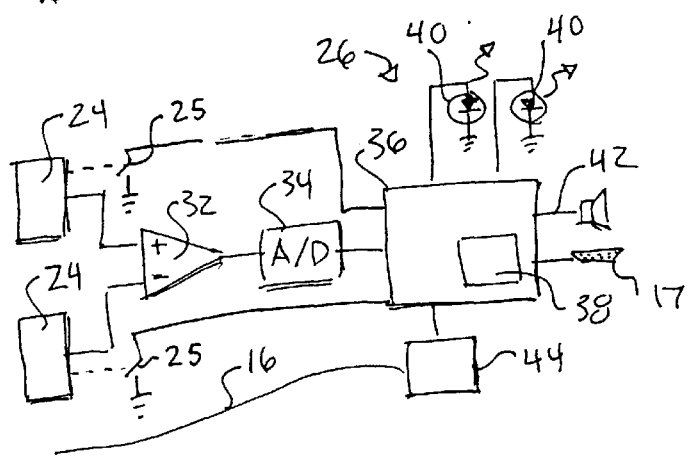
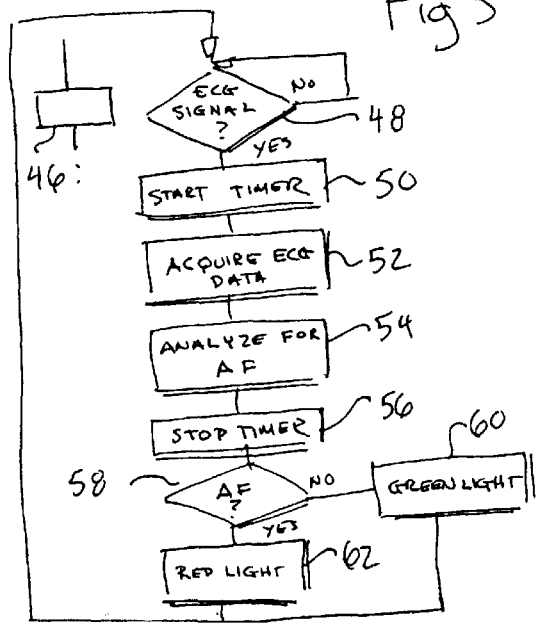
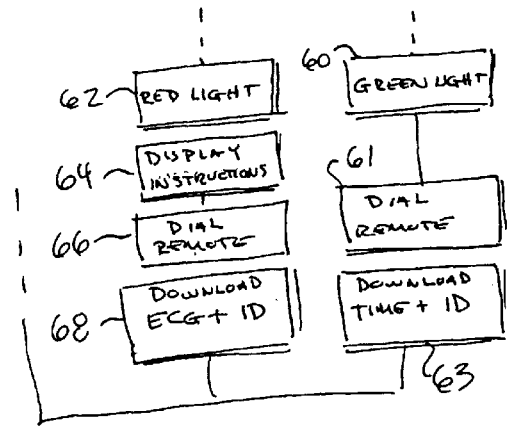

LONG TERM ATRIAL FIBRILLATION MONITOR

CROSS-REFERENCE TO RELATED APPLICATIONS

STATEMENT REGARDING FEDERALLY SPONSORED RESEARCH OR DEVELOPMENT

BACKGROUND OF THE INVENTION

The present invention relates to electronic devices for detecting atrial fibrillation and in particular to a device providing improved patient mobility and reliable long-term monitoring.

The human heart normally beats anywhere from 60 to 80 beats per minute when a person is at rest. In atrial fibrillation, the atria of the heart may beat 400 to 600 times per minute with the ventricles responding irregularly at a rate of 170 to 200 times per minute.

Diagnosis of atrial fibrillation normally requires that a qualified professional review an electrocardiograph (ECG) in which the electrical impulses from the heart are recorded and displayed in chart form. The electrical impulses are measured by electrodes attached at a number of locations to the patient's chest.

Episodes of atrial fibrillation, although serious, can be unnoticed by the patient. Yet it is desirable that atrial fibrillation be treated within 48 hours of its onset. One possible solution is the use of a "cardiac event recorder", a portable ECG recording device carried by the patient and communicating with electrodes worn under the patient's clothing and adhesively attached to the patient's skin. Such recorders may provide algorithms for monitoring the ECG signal and may report to the users that atrial fibrillation has begun. Recorders of this type may also record a rolling "window" of ECG data using solid state computer memory. In this latter case, the recorded ECG data may be transmitted over phone lines or the like for review by a qualified physician.

Unfortunately, the cardiac event recorder is not a practical tool for providing a warning of the onset of atrial fibrillation, a condition that can occur unexpectedly at any time in later life. The need for the patient to carry the cardiac event monitor about during the day and the continuous attachment of electrodes is impractical for long term monitoring that may span decades.

BRIEF SUMMARY OF THE INVENTION

The present inventors have recognized that monitoring ECG signals at a regular daily time for a brief period can reliably detect incidences of atrial fibrillation. Such regular monitoring can be provided by a unit which makes only momentary electrical contact with the patient, possibly contact with the patient's hands. An immediate evaluation of the patient's ECG signals is made, and if no atrial fibrillation is found, the patient is so informed and may go about his or her business for the remainder of the day, unencumbered by monitoring leads and equipment. The present invention thus opens the possibility of extremely long term monitoring of at risk patients with minimal intrusiveness to the patient's daily life.

Specifically then, the present invention provides a monitor for atrial fibrillation including a first and second momentary contact electrode sized to contact the patient. An atrial fibrillation detector circuit communicates with the first and second momentary contact electrodes and executes a stored program to receive an ECG signal from a patient touching the first and second momentary contact electrodes and detect a likelihood that the patient is experiencing atrial fibrillation. An output signal is provided to the patient if the likelihood is above a predetermined threshold.

Thus it is one object of the invention to provide a method for monitoring a patient for atrial fibrillation that is far less intrusive than typical cardiac evaluation monitors using chest electrodes and thus which makes long term monitoring possible.

The first and second momentary contact electrodes may be portions of handles graspable by the patient's right and left hand or may be finger pads or posts sized to contact the patient for an ECG reading.

Thus it is another object of the invention to provide for tabletop or even smaller monitor implementations the latter which may be easily carried with the patient.

The output to the patient may be an illuminating indicator indicating either that atrial fibrillation was found or not.

Thus it is another object of the invention to provide immediate feedback to the patient as to whether there is a likelihood of atrial fibrillation.

The monitor may include a recording media and the atrial fibrillation detector circuit may record the received ECG signals subsequent to the patient touching the first and second momentary contact electrodes. The ECG signals may be the patient's current ECG signals or those recorded previously during the patient's use of the device.

Thus it is another object of the invention to provide not only indication to the patient of a likely episode of atrial fibrillation, but also provide a recording of the ECG signals for review by a qualified healthcare professional.

The monitor may include a communication circuit and the atrial fibrillation detector may communicate the ECG signals to the communication circuit for transmission to a remote site.

Thus it is another object of the invention to simplify the process of reviewing the ECG signals by allowing the data to be readily communicated over communication media.

The monitor may include an alarm clock circuit providing a second output signal to the patient to remind the patient to grasp the electrodes. Further, the monitor may include a text display communicating with the atrial fibrillation detector circuit to provide text messages instructing the patient in touching the first and second momentary contact electrodes and remaining in contact with the elements prior to generation of the output signal.

Thus it is another object of the invention to provide features to simplify operation of the device and to encourage the patient in regular use of the device.

The foregoing objects and advantages may not apply to all embodiments of the inventions and are not intended to define the scope of the invention, for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

BRIEF DESCRIPTION OF THE DRAWINGS

FIG. 1 is a perspective view of an atrial fibrillation device as constructed according to the present invention showing handles for supporting electrodes to be grasped by the patient, a patient display, and connections for receiving power and communicating on the phone system;

FIG. 2 is a block diagram of the components of the atrial fibrillation monitor of FIG. 1 showing connection of the electrodes through an ECG amplifier to an analog to digital converter to be received and processed by a microcontroller having memory for storage of ECG signals;

FIG. 3 is a flow chart showing steps executed by the microcontroller of FIG. 2 in processing ECG signals from the patient;

FIG. 4 is a flow chart similar to FIG. 5 showing additional steps taken for automatically downloading ECG data to a remote location for review;

FIGS. 5a and 5b are views similar to that of FIG. 1 of an alternative embodiment for a compact atrial fibrillation device using finger pad electrodes or post electrodes instead of electrodes supported in handles;

DETAILED DESCRIPTION OF THE PREFERRED EMBODIMENT

Figure 6:
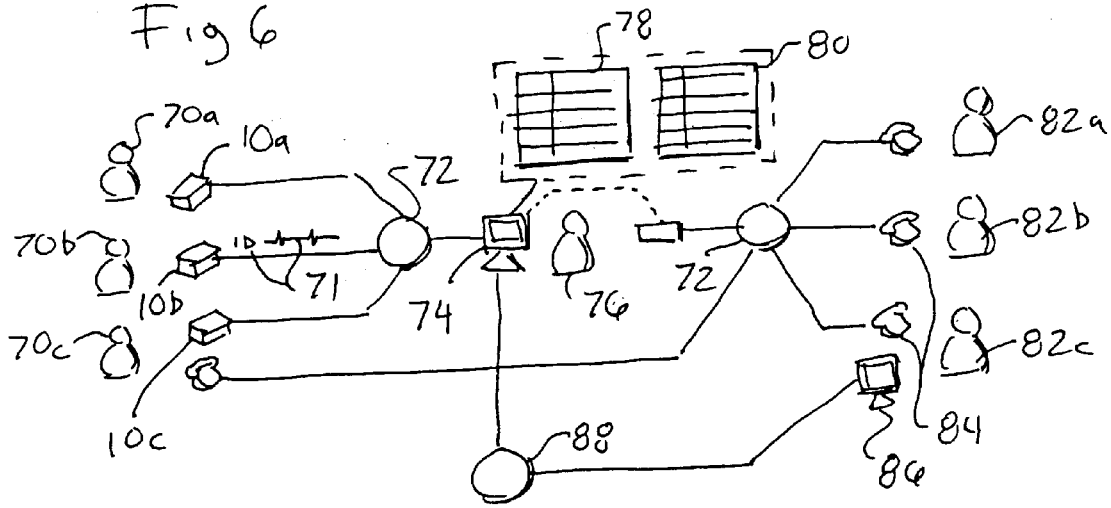
FIG. 6 is a diagram showing the path of information flow from the atrial fibrillation device to a central monitoring station for review by a qualified healthcare professional and later communication to the patient and/or the patient's physician.

Referring now to FIG. 1, an atrial fibrillation monitor 10 includes a housing 12 suitable for sitting on a tabletop, such as a nightstand or dresser. Extending from the housing 12 is a power cord 14 to be plugged into a wall outlet (not shown) and a phone line connector cord 16 to be plugged into a phone jack 18. A programming connector 17 is also provided to allow programming of the atrial fibrillation monitor 10 by a qualified healthcare professional prior to use by a patient as will be described.

The upper surface of the housing 12 includes a right and left handle, 20 and 22 respectively, providing on their undersurfaces momentary contact electrodes 24. Momentary contract electrodes 24 may be bare metal surfaces, such as stainless steel plates, and are distinguished from conventional ECG electrodes by the absence of adhesive or other methods of affixing the electrodes to the patient's skin and retaining them there. The electrodes 24 each contact one of the patient's hands when the patient grasps the left handle 20 in the patient's left hand and the right handle 22 in the patient's right hand.

An indicator light 26 is positioned on the top surface of the housing 12 to provide an indication to the patient of the condition of the patient's heartbeat. In the preferred embodiment, the indicator light 26 shows green when no irregularities are found in the patient's heartbeat and red when atrial fibrillation is detected. A grating 28 in the housing 12 may provide for communication of an audio, such as a tone or the message from an underlying speaker (not shown in FIG. 1). The audio may be used to remind the patient to take a reading or to provide instructions to the patient and/or as a redundant indication of atrial fibrillation augmenting the indicator light 26. An LCD display 30 may provide for a graphic output including text instructions to the patient as will be described below.

Referring now to FIG. 2, the electrodes 24 are received by an ECG amplifier 32 of a type well known in the art and providing for noise rejection and ground referencing of the ECG signal. The output of the ECG amplifier 32 is provided to an analog to digital converter 34 to be converted to a set of digital signals that may be received by microcontroller 36.

Microcontroller 36 combines a microprocessor with one or more input/output ports and incorporates both volatile and non-volatile memory 38, the former holding programming (as will be described below) and the latter providing a space for storing ECG signals. Two of the input/output ports are connected to red and green indicator lamps 40 providing light sources for the indicator light 26. A third input/output port is connected to a speaker or piezoelectric audio transducer 42 for providing tones or voice messages as may be appropriate to remind the patient to take a measurement of his or her heartbeat and/or to provide messages for operation of the atrial fibrillation monitor 10. A fourth set of input/output lines are connected to modem 44 which is connected to phone line connector cord 16 for communication of data over the telephone lines using standard data communication protocols. The modem may either be connected directly to the telephone lines, or may alternatively be connected to a speaker that would output acoustic signals into a telephone handset for the transmission of ECG data. While telephone lines are implemented in accordance with the preferred embodiment, it should be easily appreciated that the data transfer could be accomplished using one of many well-known alternative communication systems, such as the Internet, as will be described in more detail below. Finally, a fifth set of input/output lines is provided to the programming connector 17 such as allows programming of various parameters of operation of the atrial fibrillation monitor 10 as will be described below.

Referring now to FIG. 3, the program of the microcontroller 36 may include an alarm clock routine 46 executing in parallel with the main program to provide alarm clock type functions well known in the art and, in particular, a tone at a regular time to remind the patient to use the monitor 10. This alarm clock routine operates according to well-known algorithms and the alarm time (and current time) may be set by attaching the atrial fibrillation monitor 10 to a programming computer via the programming connector 17. Alternatively, setting controls (not shown) may be provided on top of the housing 12 in the manner of a conventional electronic alarm clock.

The program of the microcontroller 36 also executes a loop indicated by decision block 48 detecting an ECG signal such as would indicate a connection by the patient's hands to the electrodes 24. This loop may simply detect the presence of an ECG signal detected by monitoring the output of the analog to digital converter 34 or may detect a resistance drop between the electrodes using separate circuitry well known in the art.

Upon placement of the user's hands on the electrodes 24, the microcontroller 36 starts a timer as indicated by process block 50 and may provide a text display through LCD display 30 or a voice message through audio transducer 42 to the user indicating that ECG acquisition is being performed and instructing the user to retain his or her hands in position until the full elapsed time has expired. The timer value may also be displayed.

Following the starting of the timer, as indicated by process block 52, data is acquired by progressively taking samples from the analog to digital converter 34 and storing them in memory 38.

After a suitable amount of data has been collected, analyses of the ECG signal for atrial fibrillation is begun using an algorithm, as indicated by process block 54. Such algorithms are well known to those having ordinary skill in the art, such as described in U.S. Pat. No. 5,350,404, the disclosure of which is hereby incorporated by reference.

A stop timer signal, as indicated by process block 56, concludes the acquisition of ECG data and signals the patient that he or she need no longer grasp the electrodes. The time interval for the acquisition of ECG signals is normally a few minutes (e.g., five minutes) and substantially less than a day, such as would be typical for use with a cardiac evaluation monitor.

If upon completion of the analyses of the ECG signals, no atrial fibrillation was found, as determined by decision block 58, then the green indicator lamp 40 is illuminated and a text display may be provided to the patient via LCD display 30 indicating that no atrial fibrillation was found per process block 60. This outcome may be stored in memory 38 along with the ECG data and the memory 38 may hold ECG data and outcomes from previous measurements as a backup matter.

Alternatively, if atrial fibrillation was detected at decision block 58, then the program proceeds to process block 62 and the red indicator lamp 40 is illuminated indicating that atrial fibrillation has been detected by the algorithm.

With this latter indication, the patient may be instructed (or have been previously instructed) to call his or her physician and arrange for an in-office ECG to be taken.

Alternatively, as shown in FIG. 4, the microcontroller 36 may undertake additional steps after process blocks 60 and 62. Specifically, after the green light at process block 60 has been displayed, the microcontroller 36 may communicate with the modem 44 (or alternate communication system) to communicate with a central computer and report patient compliance in taking the measurement per process block 61. The transmitted data may include a time and a patient identification, the latter stored in memory 38 and preprogrammed there via the programming connector 17 prior to receipt of the trail fibrillation monitor 10 by the patient per process block 63. Optionally, the compliance signal may only be sent if a valid ECG signal was obtained.

When the red light is displayed as indicated by process block 62, instructions may be provided to the patient that data will be transmitted to a central location and the patient is to wait for a confirming phone call, per process block 64, or to call the patient's physician. At succeeding process block 66 the modem 44 or alternate communication system is activated, and at process block 68 a download of the data and the patient identification is sent to the central location. The data may be reviewed there by the patient's physician.

As described above, instead of a modem 44 linked to phone lines either directly or via an acoustic coupler, alternative communication systems may be used. For example, the ECG data may be transmitted to a personal computer for subsequent transmission to the central location via the Internet. The personal computers could further be used to store the ECG data either internally or on a storage medium such as a disc. Data may be communicated to the personal computer using one of many possible communication circuitry. For example, the atrial fibrillation monitor 10 may include a data transfer port, such as a Universal Serial Bus (USB), parallel, or serial port that is in communication with a corresponding port on the personal computer. Alternatively, the monitor may communicate with the computer via wireless communication, via, for example, an infrared communications link. Alternatively still, Bluetooth™ wireless technology may be implemented by installing a Bluetooth microchip incorporating a radio transceiver for communication with a corresponding Bluetooth microchip located in the personal computer.

Referring again to FIG. 2, the electrodes 24 may be spring loaded to recess into the housing 12 slightly when pressed and thus may serve as operators for switches 25 communicating with the microcontroller 36 to provide a signal indicating that the device is being used (detected by process block 48) or to apply power to the device in the case where it is battery operated and power must be conserved. Either or both electrodes 24 may be thus connected to switches which may also be used to indicate to the user that the necessary pressure is being applied to the electrodes 24 for good electrical contact.

Referring now to FIG. 5a, the goal of providing a convenient mechanism for long term monitoring of a patient for atrial fibrillation can also be met by a pocket sized unit having finger pads 19 also providing the electrodes 24 and operating on batteries so as to be set on a tabletop or be carried with the patient for travel. A phone connection may be provided through a direct modulation of the piezoelectric audio transducer 42 which may be held up to the telephone mouthpiece for use when the patient is at or away from home. The modulation technique in this case may be FM rather than the modem stile modulation of the modem 44 described above. The remote site may in this case include a provision for the patient providing a contact phone number at which the patient may be reached or may provide for the patient initiating a call with his or her physician or a contact number at the remote site.

Referring now to FIG. 5b, as an alternative to the finger pads 19, posts 21 may be used spaced so as to be held against the patient's chest across the heart for a reading of ECG signals.

Referring now to FIG. 6, a number of different patients 70a through 70c may each have a corresponding atrial fibrillation monitor 10a through 10c. At the regular time for patient monitoring, patient 70a through 70c may undertake the steps described above and patient identifications and/or ECG signals may be sent over the standard telephone network 72 from the atrial fibrillation monitors 10a through 10c to a central computer 74 having dial-up capabilities.

At the central computer 74, a qualified healthcare professional 76 may monitor the transmissions 71 and, communicating with a physician-patient database 78 and a compliance database 80, manually or automatically make contact with various physicians 82a through 82c via standard telephone receivers 84 or computer terminals 86, the latter communicating with a web server 88. The physician-patient database 78 includes records linking particular patients, per patient identifications loaded into the atrial fibrillation monitors 10, to physicians responsible for those patients. The physician-patient database 78 may include phone numbers and e-mail addresses of the physicians and phone numbers of the patients whose use will be described below. The compliance database 80 includes records linking patients, per their identifications, to dates on which a compliance signal was received. As will be described, the system operates to make use of one or a limited number of qualified healthcare professionals 76 to verify the judgments of atrial fibrillation algorithm of the atrial fibrillation monitors 10a through 10c so as to only call physicians 82a through 82c if required, reducing any possible false alarms.

Figure 7:
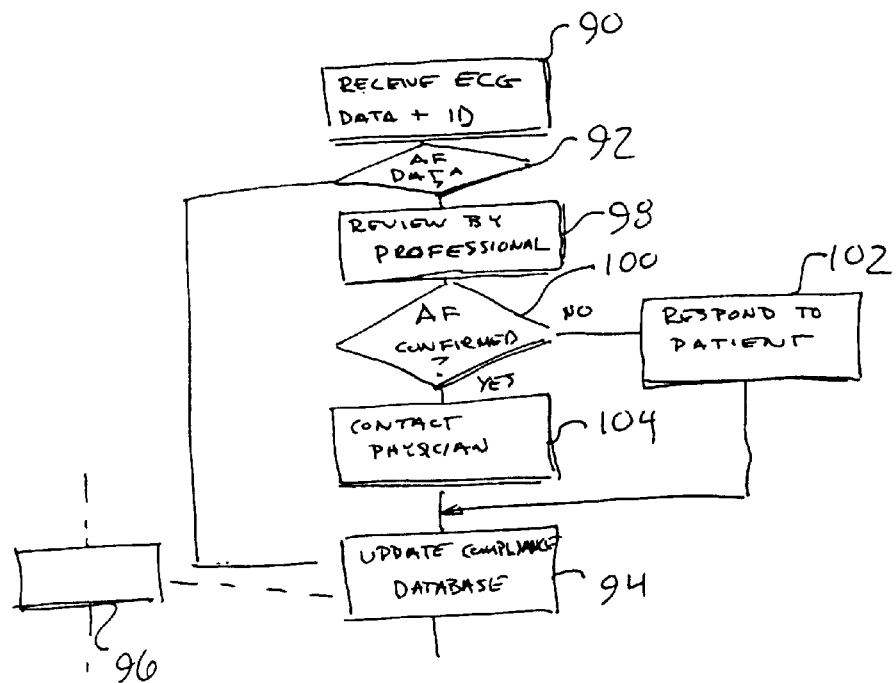
FIG. 7 is a flow chart showing operation of a computer of the central monitoring station in managing the information flow of FIG. 6.

Referring now to FIG. 7, generally, the computer 74 operates to receive ECG data and patient identification data as indicated by process block 90. At decision block 92 the data is automatically analyzed to see whether it is in response to a detection of atrial fibrillation or is simply compliance data. If the data is compliance data, then the program proceeds to process block 94 and the patient compliance database 80 is updated as indexed by the patient identification transmitted along with the compliance data.

The data of the patient compliance database 80 may be posted to the web server 88 for review by the physician typically using a password protected review process. Alternatively, or in addition, a separate program 96 may periodically review the compliance database 80 to detect whether compliance is being had and if not, to send e-mail to the appropriate physician using the patient's identification to locate the proper physician using the physician-patient database 78.

Referring again to decision block 92, if atrial fibrillation data has been sent, that is, ECG data identified by the atrial fibrillation monitor 10 as exhibiting atrial fibrillation, the ECG data is presented to the qualified healthcare professional 76 for a review as indicated by process block 98. The review may be by means of a standard computer monitor or may involve a printing out of the ECG data.

At decision block 100 the qualified healthcare professional 76 determines whether atrial fibrillation is actually present. If the qualified healthcare professional 76 concludes that the transmitted ECG data shows a normal heartbeat (and that the atrial fibrillation monitor 10 was mistaken), then the program proceeds to process block 102 and the operator is presented, based on the patient identification associated with the data being displayed, with a phone number of the patient in the physician-patient database 78. The operator may then call the patient to indicate that there was no atrial fibrillation so that the patient need no longer wait by the phone. Alternatively, this message may be generated electronically through computer techniques well known in the art upon command by the qualified healthcare professional 76.

Referring again to decision block 100, if atrial fibrillation is shown by the ECG data, after instruction by the qualified healthcare professional 76, the program proceeds to process block 104 and the qualified healthcare professional 76 is provided with the physician's phone number from the physician-patient database 78. The qualified healthcare professional 76 may then call a particular physician 82a through 82c to note that their patient has a confirmed episode of atrial fibrillation and to instruct the doctor to review the ECG signals that have been posted to the web server 88. Alternatively, or in addition, an e-mail message may be submitted to the doctor attaching the ECG data as a graphics file according to techniques well known in the art. Again, this message may be provided automatically either by synthesized voice over a standard telephone network or by e-mail message.

In this way, a machine diagnosed atrial fibrillation may be confirmed by a single highly experienced individual, shared among many patients, and a physician need only be brought into the loop when atrial fibrillation has been confirmed.

It is specifically intended that the present invention not be limited to the embodiments and illustrations contained herein, but that modified forms of those embodiments including portions of the embodiments and combinations of elements of different embodiments also be included as come within the scope of the following claims.

We claim:

1. A long-term monitor using scheduled short-term acquisition of data from a patient for determining whether a condition of atrial fibrillation exists, the monitor comprising:
    (a) a first and second momentary contact electrode for momentarily contacting the patient;
    (b) an atrial fibrillation detector circuit communicating with the first and second electrodes and executing a stored program to:
        (i) receive ECG signals from the a patient touching the first and second momentary contact electrodes;
        (ii) detect a likelihood that the patient is experiencing atrial fibrillation; and
        (iii) provide a first output signal to the patient if the likelihood is above a predetermined threshold and otherwise providing to the patient a second output signal indicating that the likelihood is not above the predetermined threshold; and
    (c) a sensor in communication with at least one of the momentary contact electrodes and the atrial fibrillation detector circuit that activates the circuit only upon a determination that the patient is touching the at least one contact electrode.

2. The monitor of claim 1 wherein the momentary contact electrodes are handles graspable by the patient's right and left hands.

3. The monitor of claim 1 wherein the momentary contract electrodes are finger pads sized to contact the patient's fingers on the left and right hand.

4. The monitor of claim 1 wherein the momentary contact electrodes are operators for switches and wherein the atrial fibrillation detector circuit communicates with the switches to monitor ECG signals only when the switches are activated by a pressing inward of the switch operators by contact with the patient.

5. The monitor of claim 1 further including an illuminating indicator and wherein the first and second outputs to the patient are different illuminations of the indicator.

6. The monitor of claim 1 further including a recording media and wherein the atrial fibrillation detector circuit further
    (iv) records the received ECG signals subsequent to the patient touching the momentary contact electrodes.

7. The monitor of claim 6 further including a communication circuit and wherein the atrial fibrillation detector circuit further
    (v) provides communication of the recorded ECG signals to communication circuit for communication to a remote site.

8. The monitor of claim 1 further including a communication circuit and wherein the atrial fibrillation detector circuit further
    (iv) communicates the ECG signals to the communication circuit for transmission to a remote site.

9. The monitor of claim 8, wherein the communication circuit further comprises a telephone line communication circuit.

10. The monitor of claim 1 further including an alarm clock circuit providing an output signal to the patient to remind the patient to contact the electrodes for a reading.

11. The monitor of claim 1 further including a text display communicating with the atrial fibrillation detector circuit to provide text messages instructing the patient in touching the momentary contact electrodes and remaining in contact with the electrodes prior to generation of the output signal.

12. A method of long term monitoring a patient for atrial fibrillation using an atrial fibrillation detector having a first and second momentary contact electrode sized to contact a portion of a patient's right and left hand, respectively, and incorporating an atrial fibrillation detector circuit communicating with the first and second momentary contact electrode, the method comprising the steps of:
    (a) sensing that the patient is touching at least one of the momentary contact electrodes;

(b) at no more than a predetermined interval, collecting from the patient an ECG sample when the patient touches the momentary contact electrodes, wherein the date is collected for a short period of time substantially less than a daily interval;

(c) detect by the atrial fibrillation detector circuit a likelihood that the patient is experiencing atrial fibrillation; and (d) provide a first signal to the patient when the likelihood is above a predetermined threshold and otherwise providing to the patient a second output signal indicating that the likelihood is not above the predetermined threshold.

13. The method of claim 12 wherein step (b) is conducted in the morning after the patient wakes.

14. The method of claim 12 wherein the atrial fibrillation monitor includes a recording media and including the further step of:

(d) recording the received ECG signals subsequent to the patient touching the first and second momentary contact electrodes.

15. The method of claim 14 wherein the atrial fibrillation monitor includes a communication circuit and further including the step of:

(e) communicating of the recorded ECG signals to a remote site.

16. The method of claim 12 wherein the atrial fibrillation monitor includes a communication circuit and further including the step of:

(d) communicating of the recorded ECG signals to a remote site.

17. The method of claim 16, wherein the communication circuit further comprises a telephone line communication circuit.

18. The method of claim 12 wherein the atrial fibrillation monitor includes a clock circuit and further including the step of:

(d) providing a second output signal to the patient at daily intervals to remind the patient to grasp the momentary contact electrodes.

19. The method of claim 12 wherein the tabletop atrial fibrillation monitor includes a text display communicating with the atrial fibrillation detector circuit and further including the steps of:

(d) providing text messages instructing the patient in touching the first and second momentary contact electrodes and remaining in contact with the elements prior to generation of the output signal.

20. A monitor for atrial fibrillation comprising:

(a) a first and second momentary contact electrode;

(b) an atrial fibrillation detector circuit communicating with the first and second electrodes and executing a stored program to:

(i) receive ECG signals from a patient touching the first and second momentary contact electrodes;

(ii) detect a likelihood that the patient is experiencing atrial fibrillation; and (iii) provide a first output signal to the patient if the likelihood is above a predetermined threshold and otherwise providing to the patient a second output signal indicating that the likelihood is not above the predetermined threshold; and (c) an alarm clock circuit providing an output signal to the patient to remind the patient to contact the electrodes for a reading.

* * * * *